(12) United States Patent
Quimby et al.

(10) Patent No.: US 7,507,336 B2
(45) Date of Patent: Mar. 24, 2009

(54) CONNECTOR FOR ANALYTICAL DEVICES

(75) Inventors: Bruce D. Quimby, Loveland, CO (US); Wesley M. Norman, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 516 days.

(21) Appl. No.: 11/111,243

(22) Filed: Apr. 20, 2005

(65) Prior Publication Data
US 2006/0237353 A1    Oct. 26, 2006

(51) Int. Cl.
*B01D 15/08* (2006.01)
(52) U.S. Cl. .................... 210/198.2; 210/656; 422/103; 96/106
(58) Field of Classification Search ............... 210/198.2, 210/656; 422/103; 73/61.56; 285/18; 96/106
See application file for complete search history.

(56) References Cited

U.S. PATENT DOCUMENTS

| | | | | |
|---|---|---|---|---|
| 3,978,575 | A | * | 9/1976 | Beyer et al. ................. 29/426.4 |
| 4,227,617 | A | * | 10/1980 | Albrecht et al. ............. 215/251 |
| 4,280,905 | A | * | 7/1981 | Gunkel et al. ............ 210/198.2 |
| 4,451,364 | A | * | 5/1984 | Higgins et al. ........... 210/198.2 |
| 4,649,124 | A | * | 3/1987 | Hall ............................ 436/150 |
| 4,676,084 | A | * | 6/1987 | Signorelli .................... 70/440 |
| 4,719,011 | A | * | 1/1988 | Shalon et al. ............. 210/198.2 |
| 4,787,656 | A | | 11/1988 | Ryder |
| 4,792,396 | A | * | 12/1988 | Gundelfinger ........... 210/198.2 |
| 4,799,717 | A | * | 1/1989 | Kingsford ................... 285/341 |
| 4,966,550 | A | * | 10/1990 | Privat ........................... 433/25 |
| 5,163,215 | A | | 11/1992 | Ledford, Jr. |
| 5,169,522 | A | * | 12/1992 | Shalon et al. ............. 210/198.2 |
| 5,517,740 | A | | 5/1996 | Costlow et al. |
| 5,582,723 | A | * | 12/1996 | Boone et al. ............. 210/198.2 |
| 5,589,063 | A | * | 12/1996 | Sanford et al. ........... 210/198.2 |
| 5,656,034 | A | * | 8/1997 | Kochersperger et al. .... 604/155 |
| 5,667,676 | A | * | 9/1997 | Alaska ..................... 210/198.2 |
| 5,926,675 | A | | 7/1999 | Miyano et al. |
| 5,954,375 | A | * | 9/1999 | Trickle et al. ................ 285/342 |
| 6,102,449 | A | | 8/2000 | Welsh |
| 6,131,963 | A | * | 10/2000 | Williams et al. ............. 285/343 |
| 6,572,155 | B2 | | 6/2003 | Dehmer |
| 6,709,027 | B2 | | 3/2004 | Rittenhouse |
| 7,316,777 | B2 | * | 1/2008 | Loy, Jr. ..................... 210/198.2 |
| 2002/0117855 | A1 | | 8/2002 | Rittenhouse |
| 2004/0108718 | A1 | | 6/2004 | Rittenhouse |
| 2004/0113429 | A1 | * | 6/2004 | Williams et al. ......... 285/382.7 |
| 2006/0169628 | A1 | * | 8/2006 | Loy, Jr. ..................... 210/198.2 |

OTHER PUBLICATIONS

Kirby et al. "Microfluidic Routing of Aqueous and Organic Flows at High Pressures: Fabrication and Characterization of Integrated Polymer Microvalve Elements," The Royal Society of Chemistry, Lab Chip (2005) 5:184-190.

* cited by examiner

*Primary Examiner*—Ernest G Therkorn
(74) *Attorney, Agent, or Firm*—Marc Bobys

(57) ABSTRACT

A connector element for use with analytical devices is provided. The connector element includes a cavity for receiving a sealing member, and an access element for providing access to the sealing member when disposed in the cavity, e.g., for dislodging the sealing member from the connector element. Also provided are analytical devices that include the connector element, as well as methods of using the same.

18 Claims, 2 Drawing Sheets

CONNECTOR FOR ANALYTICAL DEVICES

BACKGROUND OF THE INVENTION

Chromatographic apparatuses used for both gas and liquid chromatography typically employ capillary columns to provide control passageways for substances to be analyzed. Areas of analytical application for capillary columns include gas chromatography, liquid microbore chromatography, capillary electrophoresis, and supercritical fluid chromatography. In many analytical applications today, glass, metal or flexible fused silica capillary columns are used. Occasionally, polymeric capillaries are also used.

In many analytical chromatographic applications in which a chromatographic column, such as a capillary column, is employed, the column ends must be connected, e.g., to a sample injector and a detector of a chromatographic device, to another column, etc. Connectors are known in the art for receiving a fluid stream in a first fluid-bearing conduit (such as a column) and then delivering the received fluid stream to a second fluid-bearing conduit (such as may be found in a detector, in a second column, etc.). The fluid connection may be obtained by manual alignment and coupling of separate components that comprise the connector, such as by alignment and compression of a sealing device onto a tubular device while being fitted to a receiving fitting.

The sealing device on conventional connectors is typically a ferrule having a conical frustrum exterior and a through hole. The tubular device, such as a column, or connecting tube, is inserted into the through hole and the tubular device/ferrule assembly is then inserted into a receiving feature, e.g., of an injector or detector or union or fluidic manifold of a chromatographic system, which is shaped as a complementary conical frustrum. The receiving feature is referred to as the ferrule seat. The tubular device/ferrule assembly is then forced into the ferrule seat via pressure, e.g., as may be applied by a threaded fastener, to provide a seal between the ferrule and ferrule seat.

Good laboratory practice dictates that, upon replacement or reinstallation of a column, the ferrule should be replaced. However, replacement is often a difficult or tedious procedure. For example, the ferrule in the connector may have become seized and are difficult or impossible to remove. Sometimes, prying tools or screw extractors are employed in order to obtain sufficient purchase to remove the ferrule from the cavity. In yet other instances, a thermal shock process may be employed to dislodge the ferrule. However, such process can damage the interior of the connector. Thus, a routine column removal, replacement, or installation task becomes an expensive and time-consuming process, which can harm other components of the system, such as receiving elements of injectors or detector of the system.

As such, there is interest in the development of an approach to easily remove stuck ferrules, or analogous structures such as plugs, from connector interiors, such as ferrule seats, e.g., of injectors and detectors in chromatographic systems. The present invention satisfies this need.

RELEVANT LITERATURE

Publications of interest include U.S. Pat. Nos. 5,163,215; 6,102,449; 6,572,155 and 6,709,027; as well as published U.S. Patent Application Nos. 2004/0108718 and 2002/0117855.

SUMMARY OF THE INVENTION

A connector element for use with analytical devices is provided. The connector element includes a cavity for receiving a sealing member, and an access element for providing access to the sealing member when present in the cavity. Also provided are analytical devices that include the connector element, as well as methods of using the same.

BRIEF DESCRIPTIONS OF THE FIGURES

FIG. 1 provides a representation of a connector element according to one embodiment of the invention.

DEFINITIONS

Figure 1:
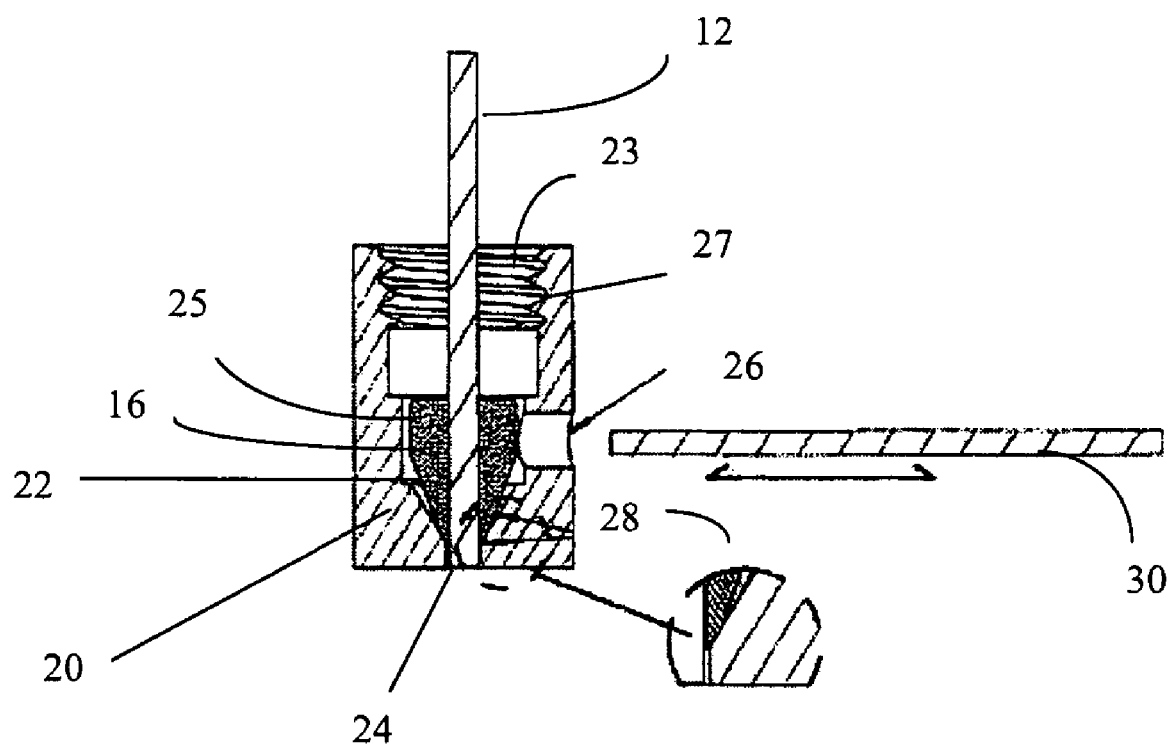

Unless defined otherwise, all technical and scientific terms used herein have the same meaning as commonly understood by one of ordinary skill in the art to which this invention belongs. Still, certain elements are defined below for the sake of clarity and ease of reference.

The term "nut" refers to a perforated block, usually of metal, that has an internal or external screw thread and is used for tightening or holding an object in a fixed position relative to another object and the nut.

A "channel" refers to any type of fluid conduit, such as a tubular passageway.

A "fluid conduit" refers to a device that serves to transfer a volume of fluid, e.g., a gas or liquid, from a first to a second location. In certain embodiments, fluid conduits are chromatographic devices, such as chromatographic columns. Chromatographic columns are known in the art, and may be capillary chromatographic columns.

A "fluid seal" refers to a "closure" that is substantially, if not completely, impermeable to fluids, including both liquids and gases. A "liquid seal" refers to a "closure" that is substantially, if not completely, impermeable to liquids. A "gas seal" refers to a "closure" that is substantially, if not completely, impermeable to gases. "Optional" or "optionally" means that the subsequently described circumstance may or may not occur, so that the description includes instances where the circumstance occurs and instances where it does not.

A "plastic" is any synthetic organic polymer of high molecular weight (for example at least 1,000 grams/mole, or even at least 10,000 or 100,000 grams/mole.

An item is considered to be "flexible" if it can be bent 180 degrees around a roller of less than 1.25 cm in radius. The item can be so bent and straightened repeatedly in either direction at least 100 times without failure (for example, cracking) or plastic deformation. This bending must be within the elastic limits of the material. The foregoing test for flexibility is performed at a temperature of 20° C.

An item is "rigid" if it is not flexible, and is constructed such that a segment about 2.5 by 7.5 cm retains its shape and cannot be bent along any direction more than 60 degrees (and often not more than 40, 20, 10, or 5 degrees) without breaking.

"Fluid tight" is used herein to describe the spatial relationship between two solid surfaces in physical contact, such that fluid (liquid and/or gas) is prevented from flowing into the interface between the surfaces.

The terms "Compliant" and "Deformable" are employed interchangeably and refer to a material that is able to be compressed e.g., to conform to a contacted surface.

"Chromatographic" processes generally include preferential separations of components, and include gas phase, liquid phase, gas solid, gas liquid, solid phase, reverse-phase, hydrophobic interaction, ion exchange, molecular sieve chromatography, affinity chromatography and like methods.

"Gas chromatographic analysis" refers generally to an analysis wherein an inert carrier gas is passed through a temperature-controlled column which contains a stationary phase in the form of porous sorptive media, or through a hollow capillary coated with the stationary phase. A sample of the subject mixture is injected into the carrier gas stream and passed through the column. As the subject mixture passes through the column, it separates into its various components. A detector, positioned at the outlet end of the column, detects each of the separated components contained in the carrier fluid as they exit the column.

"Detector" refers to an element that outputs a signal that may be data or converted to data. In representative embodiments, the detector may provide a sample peak data representative of information useful as a chromatogram, and includes a wide variety of useful chromatographic detectors, such as the flame ionization detector (FID), photoionization detector (PID), nitrogen phosphorus detector (NPD), flame photometric detector (FPD), thermal conductivity detector (TCD), atomic emission detector (AED), electrolytic conductivity detector (ELCD), and electron capture detector (ECD). Mass spectral detectors, such as Ion Traps, Inductively Coupled Plasma, etc., as well as infrared spectral detectors are compassed within the scope of the term "detector". Also encompassed are liquid phase chromatographic detectors, e.g., ultraviolet (UV-VIS) detectors, refractive index reflectors, electrochemical detectors, fluorescent detectors, mass spectrometers, etc.

The terms "assessing" and "evaluating" are used interchangeably to refer to any form of measurement, and include determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

"Communicating" information references transmitting the data representing that information as signals (e.g., electrical, optical, radio signals, and the like) over a suitable communication channel (e.g., a private or public network).

"Forwarding" an item refers to any means of getting that item from one location to the next, whether by physically transporting that item or otherwise (where that is possible) and includes, at least in the case of data, physically transporting a medium carrying the data or communicating the data.

By "remote location" it is meant a location other than the location at which an object is present or an event occurs. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles (or more) apart.

A "computer", "processor" or "processing unit" are used interchangeably and each references any hardware or hardware/software combination which can control components as required to execute recited steps. For example a computer, processor, or processor unit includes a general purpose digital microprocessor suitably programmed to perform all of the steps required of it, or any hardware or hardware/software combination which will perform those or equivalent steps. Programming may be accomplished, for example, from a computer readable medium carrying necessary program code (such as a portable storage medium) or by communication from a remote location (such as through a communication channel).

A "memory" or "memory unit" refers to any device which can store information for retrieval as signals by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

DETAILED DESCRIPTION OF THE INVENTION

A connector element for use with analytical devices is provided. The connector element includes a cavity for receiving a sealing member, and an access element for providing access to the sealing member when disposed in the cavity. Also provided are analytical devices that include the connector element, e.g., as part of an injector or detector element, as well as methods of using the same.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All patents and publications mentioned herein are incorporated herein by reference to disclose and describe the methods and/or materials in connection with which the publications are cited. The citation of any patent or publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

As summarized above, aspects of the invention include connectors for making fluid connections between a fluid conduit and a receiving element, such as a detector or injector of a chromatographic system. The connector elements of the present invention generally include a bore having first and second ends, where the first and second ends have different cross-sectional dimensions. The outer dimensions of the connector element may vary depending on the particular application in which the element is employed (e.g., as a receiver for an injector or detector of a chromatographic system). In representative embodiments where the connector element is configured to provide a connection between a column and a chromatographic device, the connector element will have a length ranging from about 1 mm to about 45 mm, such as from about 8 mm to about 10 mm. Where the connector has a tubular configuration, the outer diameter of the connector (in lieu of the width and height ranges above) may range from about 1 mm to about 15 mm such as from about 2 mm to about 6.5 mm.

As indicated above, the first and second ends of the bore of the connector element have different internal cross-sectional dimensions, e.g., diameters, where the internal cross-sectional dimension or diameter of the first end of the bore may be at least about 1.2 fold, such as at least about 4 fold longer than the internal cross-sectional dimension of the second end of the bore. In representative embodiments, the internal cross-sectional dimension (e.g., diameter) at the first end of the bore ranges from about 3.2 mm to about 15 mm, such as from about 3 mm to about 3.2 mm, while the internal cross-sectional dimension (e.g., diameter) at the second end of the bore may range from about 0.8 mm to about 6.5, such as from about 0.8 mm to about 1 mm.

The first end of the subject connectors defines a boundary or edge of a portion of the bore that is configured as a cavity dimensioned to receive a sealing member, e.g., a ferrule or plug. In representative embodiments, cavity portion of the bore of the connector element is configured to make a fluid-tight seal with a sealing member, such as a ferrule, disposed around a fluid conduit, e.g., column. As is known in the art, where the sealing member is a ferrule, the ferrule may have a conical frustrum exterior and a through hole or central bore. In certain embodiments, the ferrule is provided with an aft end having aft transverse surface that is perpendicular to the central axis of the bore, and a forward end having a frustoconical tapered portion, wherein the central bore extends therebetween for receiving the column and for aligning the ferrule with respect to the exterior surface of the column. The central bore is sized and shaped for a snug but nonetheless slidable fit to the exterior of the capillary tube or column. In these embodiments, the cavity is shaped to accommodate this ferrule/column assembly and is conveniently referred to as a ferrule seat. It should be noted that while the present discussion focuses for ease of description primarily on the sealing member being a ferrule, the sealing member may also be a plug or other structure configured to be placed in the cavity and produce a seal.

As is known in the art, during use the sealing member is urged against the cavity wall under pressure. Because the applied pressure, a portion of the sealing member is compressed tight against a region of the cavity wall and thereby provides a fluid-tight seal at the region of the cavity wall. This region is referred to herein as a sealing region or location of the cavity wall.

A feature of the connectors is that they include an access element positioned in a side of the connector element that provides access to a side of a sealing member when disposed in the cavity of the connector. The access element is typically a through passage or bore in the side of the connector, where the passage provides for access by a dislodgement element, e.g., a rigid rod or analogous device, from a location outside of the connector to a sealing member present in the cavity of the connector element.

The dimensions of this access element may vary, as long as they are sufficient to provide for the desired access of a dislodgement element to the sealing member when present in the cavity. In representative embodiments, the access element is a passageway having a cross-sectional dimension, e.g., diameter, ranging from about 0.5 mm to about 3 mm, such as from about 1 mm to about 1.7 mm.

The location of the access element is, in representative embodiments, at a position on the connector that is other than the sealing region or location where the sealing member, when present in the cavity, is urged against the cavity wall to make a seal. In representative embodiments, the access element is positioned at a location that is sufficiently far from the sealing location to provide sufficient leverage and yet on the side of the ferrule, e.g., from about 0.9 mm to about 1.2 mm from the sealing location or region of the cavity.

The connector element may further include a mating element for engaging a corresponding element associated with the fluid conduit, such that the fluid conduit may be stably engaged with the connector element. For example, the fluid conduit may be disposed within a bore of a nut having threads at one end, and the connector element may have threads for engaging the threads on the nut to thereby secure the fluid conduit to the connector element, as well as apply pressure on the sealing member to urge it against the cavity of the connector element. In certain of these embodiments, the threads are generally positioned proximal to the first end of the connector element, and may be internal or external threads, where in certain embodiments internal threads are positioned in the wall of the cavity.

The connector element of the subject invention may be fabricated from a variety of different materials, including but not limited to: metals, such as stainless-steel.

As reviewed above, the connector element is suitable for use in connecting a first fluid conduit, such as a column, to a receiver element (e.g., such as may be found on an injector or detector of a chromatographic system, a second column, a fluid manifold, etc.) in a fluid tight seal. In representative embodiments, the connector element is one that provides for a fluid tight connection between a fluid conduit, such as a capillary column or tube, with a receiver of an analytical device, such as a chromatographic device, e.g., a liquid or gas chromatographic device. For example, the connector element may be configured for use with a receiver of a gas chromatographic device, e.g., an injector, a detector, a fluid manifold, e.g., as may be found in a splitter, Dean's switch etc., a second fluid conduit, e.g., column, etc.

In further describing aspects of the invention, a representative connector element will now be described that is suitable for use with gas chromatographic analytical devices. FIG. 1 provides a representative embodiment of a connector element according to the subject invention that is part of an injector or detector interface for a capillary column of a gas chromatographic device. FIG. 1 shows capillary column 12 disposed within the central bore of ferrule 16.

Also shown in FIG. 1 is connector element 20 that has a central bore 22 terminating at first end 23 and second end 24. Central bore 22 provides an internal cavity 25 that has a frustrum configuration adapted to substantially, though not completely, mate with the frustrum shape of the ferrule 16. Also shown is access element 26 that is dimensioned to provide access for a dislodgement element 30 (represented as a rigid rod) to a ferrule present in the cavity, i.e. ferrule seat. Also shown are internal threads 27 that engage the threads of a retainer nut (not shown) when present in the cavity.

As shown in FIG. 1, the column (12)/ferrule (16) assembly is positioned in the internal cavity 22 or ferrule seat of connector element 20. As shown, the capillary column 12 is inserted into the through hole of the ferrule 16, and the resultant capillary column/ferrule assembly is then inserted into the cavity 25 of the connector element, where the cavity or ferrule seat is shaped as a complementary conical frustrum. As shown, the capillary column/ferrule assembly has been forced into the ferrule seat, and pressure has been applied, e.g., via pressure applied by a threaded fastener using threads 27, to produce a seal between the ferrule and cavity wall (e.g., ferrule and ferrule seat) at a sealing location or region 28.

Figure 2A:
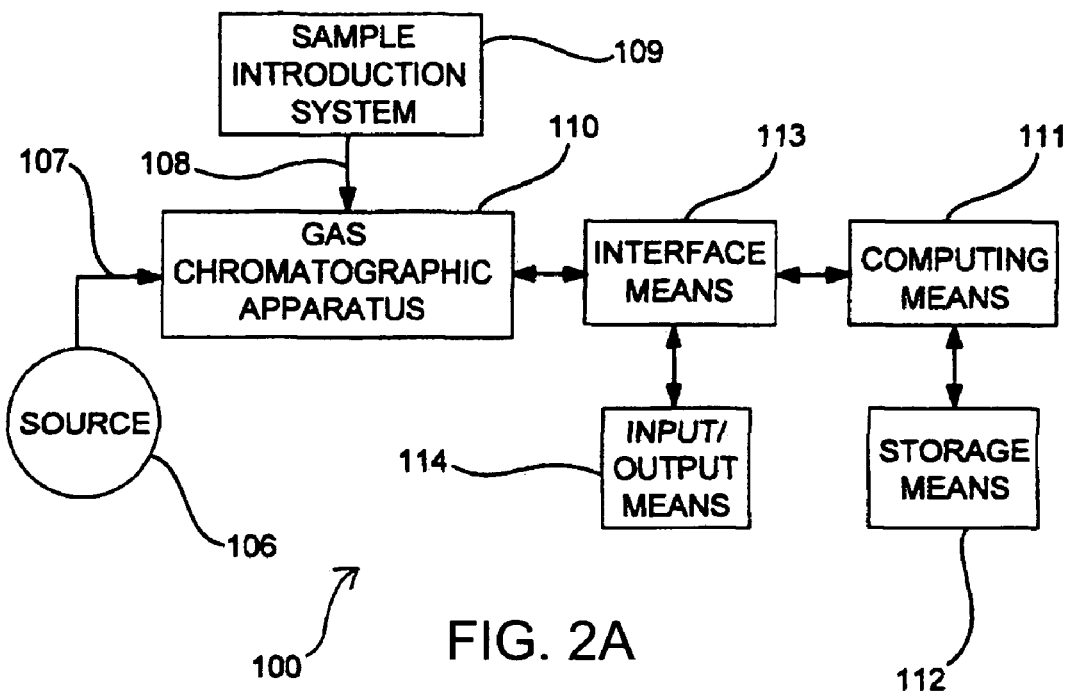
FIG. 2A is an exemplary block diagram of an analytical apparatus according to the subject invention.
Figure 2B:
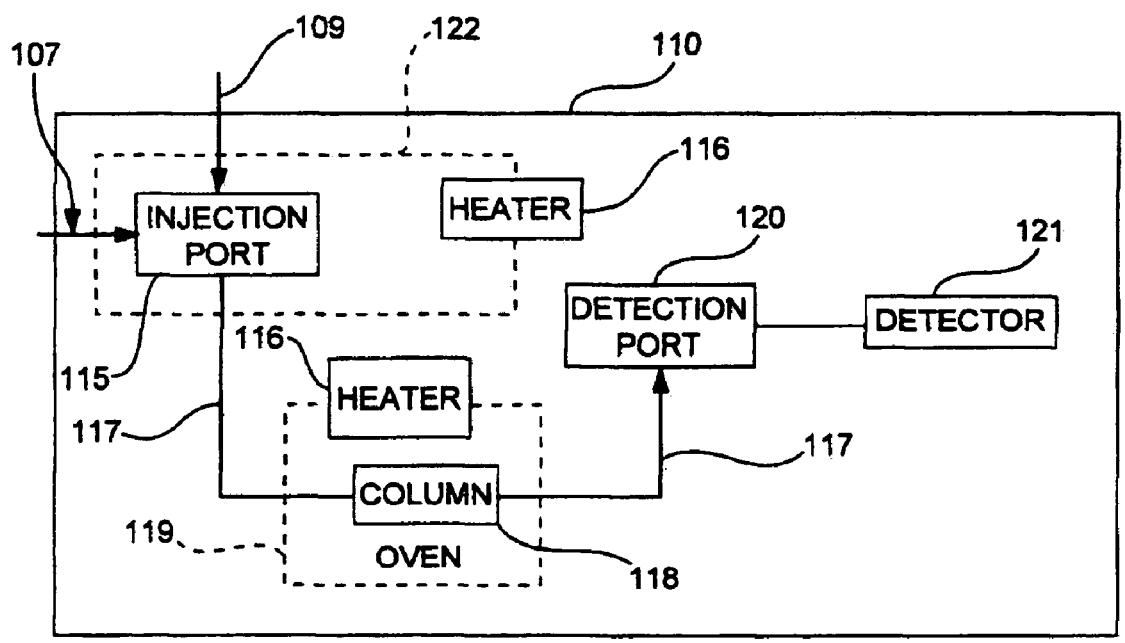
FIG. 2B is an exemplary block diagram of a chromatographic apparatus which may be utilized with the apparatus of FIG. 1 according to the subject invention.

The connector element depicted in FIG. 1 is part of a gas chromatographic device or system 100 as shown in FIGS. 2A and 2B. The system 100 includes sample introduction system 109, a chromatographic apparatus 110, computing means 111, storage means 112, interface means 113, and input/output means 114. In order to perform a chromatographic separation of a sample introduced on line 108, a quantity of the sample is injected into a fluid stream, e.g., in the form of a pressurized carrier gas, via sample inlet 122 having an injection port 115 that is supplied with a carrier gas stream. The carrier gas is supplied on source line 107 to the inlet 122 from a source 106. The carrier gas may include one or more component gases—such as, for example, hydrogen, nitrogen, or helium—depending upon the particular chromatographic separation to be performed.

Sample inlet 122 provides a portion of the sample/carrier gas mixture to a separation column 118, via an injector element that includes a connector element as shown in FIG. 1. In certain embodiments, the column 118 may be positioned within a temperature-controlled thermal chamber, or oven 119, or within or around a resistively heated column or an integrated peltier heated and cooled column, for example. The inlet 122 and the oven 119 (if provided) may be temperature controlled, e.g., by way of respective heaters 116. In order to ensure that the temperature within the oven 119 is at a desired level, the temperatures in the inlet 122 and oven 119 may be provided to interface 113 and the computing means 111. The heaters 116 may maintain controlled temperatures in the inlet 122 and oven 119 in response to control signals generated by the computing means 111. The carrier gas/sample combination passing through the column 118 on line 117 may thereby be exposed to a temperature profile. The temperatures may be controlled according to a selected program so that the sample will separate into its components.

As the carrier gas (containing the sample) exits the column 118, the outflow passes into detector 121 via a receiver that includes a connector as depicted in FIG. 1, where the presence of one or more sample constituent components is detected by a detector 121. The detector 121 can be any of the GC detectors known in the art, so long as it is capable of determining at least one property (e.g., such as a physicochemical property) of the sample components which exit the column 118. The detector output signal may then be received by the processor 111 and optionally stored in the storage element 112. The detector output signal may be provided in the form of data representative of a series of sample peaks in at least one sample peak series. The sample peaks may be identified and presented in one or more sample peak series. Each sample peak series may be analyzed with aid of a peak identification method based on data representative of one or more selected standard peak groups. Data representative of the standard peak group(s) may be predetermined or inputted at the input/output element 114 and stored in the storage element 112.

The processor 111 may include computing devices amenable to the practice of this invention, e.g., one or more computing devices such computers, microprocessors, micro controllers, switches, logic gates, or any equivalent logic device capable of performing the functions required of it. Processor 111 may be coupled with interface element 113 and information input/output element 114; the latter may include a keyboard, keypad, or computer mouse, or remote processor (not shown) for inputting operating condition parameters, system data, and the like. Information input/output element 114 may include display means such as an alphanumeric or video display, a printer, or the like. The processor 111 may further include storage element 112 in the form of volatile and non-volatile memory devices in which input and output information, operating condition parameters, system information, and programs may be stored and retrieved. Operating commands, device and fluid type information, detector response attributes, column temperature programs, and other information necessary to perform a chromatographic analysis may be entered into the processor 111 by way of the input/output element 114 or retrieved from storage element 112. Messages prompting the user to enter certain information, such as a desired operating parameter, may be generated by the processor 111 and displayed on the display. The interface element 113 may further include network and bus system (input/output or I/O) controllers, isolation devices, clocks, and other related electronic components for performing control, processing, and communication tasks other than those described herein.

The subject connector elements may be used in receivers of any number of analytical devices, such as chromatographic devices, including both liquid and gas chromatographic devices. Of interest are connector elements configured for use with the following representative analytical systems: Agilent Technologies GC or GC/MS systems, including 6890N GC, 5973 Inert MSD, 5973N GC/MS, 6850 Series II Network GC and 6850 Series Network GC, 3000 Micro GC, 6820 GC, 6890 Micro ECD, etc. Aspects of the subject invention include connector elements adapted for retrofitting existing device systems.

While exact protocols for using the subject connectors will vary greatly, in representative embodiments the connectors employed, as indicated above, for making a fluid tight connection between a fluid conduit, such as a column, and a receiving element, e.g., an injector or detector, of an analytical device. In a representative application in which the connectors are part of receiving elements for capillary columns, a nut and ferrule are first slipped over the end of a capillary column. Following insertion through the ferrule, the operator cleaves a small length of capillary column from the end of the column to be sure the operative column end is open and free of small particles or ferrule shavings which would obstruct the flow of mobile phase during chromatographic separation. The operator then gathers the nut and ferrule together along the length of the column, and draws the end of the column into proximity to the forward end of the ferrule. The nut/ferrule/ column combination is then inserted into, for example, an injector port of a capillary gas chromatograph. The nut is then tightened. This procedure is repeated for the other end of the column, which is sealed into a detector port.

As reviewed above, following column use and removal, the ferrule may become lodged or stuck in the receiving element, e.g., of the injector or detector. In such instances, a dislodgement member, such as a rigid rod, is then passed through the access element of the connector element to apply force to the side of the ferrule stuck in the ferrule seat. The force that is applied to the ferrule is sufficient to overcome the sealing forces and thereby dislodge the ferrule from the ferrule seat.

A new column may then be introduced into the system, as desired.

Finally, kits are also provided. The subject kits may include a connector element as described above. Kits may also include a dislodgement member, such as a rigid rod or analogous structure, configured to pass through the access element of the connector to dislodge a stuck ferrule therein. In embodiments in which a plurality of fluid elements are provided, the elements may be packaged together or in separate compartments of the kit.

The subject kits may also include written instructions for using the components of a kit, e.g., for installing a connector element on a device and/or using a dislodgement member therewith. Instructions of a kit may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

In certain embodiments of the subject kits, the components of the kit are packaged in a kit containment element to make a single, easily handled unit, where the kit containment element, e.g., box or analogous structure, may or may not be an airtight container.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A connector for an analytical instrument, said connector comprising:
    a sealing member configured to receive a fluid conduit;
    a connector element having first and second ends of different cross sectional dimensions, the connector element including:
        (a) a cavity wall defining a cavity dimensioned to receive the sealing member so that an end portion of the sealing member contacts the cavity wall in a sealing region of the cavity wall to form a seal between the cavity wall and the sealing member, and a side of the sealing member is spaced apart from the cavity wall when the sealing member is fully seated in the cavity;
        (b) an access hole positioned in a side of said connector element and spaced apart from the sealing region, that provides access to the side of the sealing member when the sealing member is disposed in said cavity to allow an external dislodging tool to pass through the connector element and contact the sealing member to overcome sealing forces between the cavity wall and the sealing member and thereby dislodge the sealing member when the sealing member is lodged or stuck in the connector element; and
        (c) an external dislodging tool sized and dimensioned to pass through said access hole.

2. The connector according to claim 1, wherein said sealing member is disposed around said fluid conduit.

3. The connector according to claim 2, wherein said sealing member is a ferrule.

4. The connector according to claim 1, wherein said sealing member is a plug.

5. The connector according to claim 1, wherein said connector element is coupled to a receiver of said analytical device.

6. The connector according to claim 5, wherein said receiver is for an injector, detector, second fluid conduit or fluid manifold.

7. The connector according to claim 5, wherein said analytical device is a chromatographic device.

8. The connector according to claim 7, wherein said chromatographic device is a liquid chromatographic device.

9. The connector according to claim 7, wherein said chromatographic device is a gas chromatographic device.

10. The connector according to claim 1, wherein:
    an outer surface of the end portion of the sealing member is disposed at a first acute angle in relation to a centerline of the sealing member; and
    the portion of the cavity wall that contacts the end portion of the sealing member is disposed at a second acute angle in relation to a centerline of the connector element, the second acute angle being greater than the first acute angle.

11. The connector according to claim 10, wherein the end portion of the sealing member and the portion of the cavity wall that contacts the end portion of the sealing member are each shaped as a truncated cone.

12. The connector according to claim 1, wherein the access hole extends between an outer surface of the connector element and the cavity wall.

13. The connector according to claim 1, wherein: the end portion of the sealing member is tapered; a portion of the cavity wall is tapered; and the taper of the end portion of the sealing member differs from the taper of the portion of the cavity wall.

14. The connector according to claim 13, wherein the taper of the end portion of the sealing member differs from the taper of the portion of the cavity wall so that the cavity wall diverges from the sealing member over a portion of the length of the connector element.

15. The connector according to claim 1, wherein a portion of the sealing member is capable of moving in relation to the connector element a direction substantially perpendicular to a direction of insertion of the sealing member in the connector element when the sealing member is fully seated in the cavity.

16. The connector according to claim 15, wherein the portion of the sealing member is capable of moving in relation to the connector element the direction substantially perpendicular to a direction of insertion of the sealing member in the connector element when the sealing member is fully seated in the cavity in response to insertion of a dislodging tool through the access opening and into the cavity.

17. A connector comprising:
a ferrule configured to receive a fluid conduit;
a connector element having first and second ends of different cross sectional dimensions, the connector element including:
(a) a ferrule seat dimensioned to receive an end portion of the ferrule so that the end portion contacts the ferrule seat in a sealing region of the ferrule seat to form a seal between the ferrule seat and the ferrule, wherein a side of the ferrule is spaced apart from a side of the connector element when the end portion is seated in the ferrule seat;
(b) an access hole positioned in the side of said connector element and spaced apart from the sealing region, that provides access to the side of the ferrule when the ferrule is present in said ferrule seat to allow an external dislodging tool to pass through the connector element and contact the ferrule to overcome sealing forces between the ferrule seat and the ferrule and thereby dislodge the ferrule when the ferrule is lodged or stuck in the ferrule seat; and
(c) an external dislodging tool sized and dimensioned to pass through the access hole.

18. A connector for an analytical instrument comprising:
a plug configured to receive a fluid conduit;
a connector element having first and second ends of different cross sectional dimensions, the connector element including:
(a) a cavity wall defining a cavity dimensioned to receive the plug so that an end portion of the plug contacts the cavity wall in a sealing region of the cavity wall to form a seal between the cavity wall and the plug, and a side of the plug is spaced apart from the cavity wall when the plug is fully seated in the connector element;
(b) an access hole positioned in a side of said connector element and spaced apart from the sealing region, that provides access to the side of the plug when the plug is disposed in said cavity to allow an external dislodging tool to pass through the connector element and contact the plug to overcome sealing forces between the cavity wall and the plug and thereby dislodge the plug when the plug is lodged or stuck in the connector element; and
(c) an external dislodging tool sized and dimensioned to pass through the access hole.

* * * * *